United States Patent [19]

Helms et al.

[11] Patent Number: 4,678,917

[45] Date of Patent: Jul. 7, 1987

[54] INSTANTANEOUS READING MULTICHANNEL POLYCHROMATIC SPECTROPHOTOMETER METHOD AND APPARATUS

[75] Inventors: Charles C. Helms, Trumbull; Ralph D. Conlon, Wilton; Edward B. Delany, Ridgefield, all of Conn.

[73] Assignee: The Perkin-Elmer Corporation, Norwalk, Conn.

[21] Appl. No.: 703,260

[22] Filed: Feb. 19, 1985

[51] Int. Cl.[4] ............................................. G01J 3/36
[52] U.S. Cl. ............................... 250/373; 250/461.1; 356/317; 356/328
[58] Field of Search .................... 250/373, 372, 461.1; 356/328, 326, 308, 319, 317

[56] References Cited

U.S. PATENT DOCUMENTS

| | | | |
|---|---|---|---|
| 3,973,118 | 8/1976 | LaMontagne | 250/209 |
| 3,985,441 | 10/1976 | Schoeffel et al. | 356/310 |
| 4,060,327 | 11/1977 | Jacobowitz et al. | 356/332 |
| 4,097,152 | 6/1978 | Kishner | 356/300 |
| 4,140,394 | 2/1979 | Roos | 356/328 |
| 4,320,971 | 3/1982 | Hashimoto et al. | 356/334 |
| 4,523,096 | 6/1985 | Yasuda et al. | 250/461.1 |
| 4,544,271 | 10/1985 | Yamamoto | 356/328 |
| 4,568,186 | 2/1986 | Yoshimura et al. | 356/328 |

OTHER PUBLICATIONS

Borman, "Charge-Coupled Diode Array Detectors for LC", Anal. Chem., 55(8), Jul. 1983, pp. 836A-842A.

Primary Examiner—Carolyn E. Fields
Attorney, Agent, or Firm—Ronald G. Cummings; Francis L. Masselle; Edwin T. Grimes

[57] ABSTRACT

A beam of radiation is directed into a liquid sample cell containing a sample to be analyzed in solution. The illumination emanating from the sample cell as a result of the beam of radiation from the radiation source is diffracted into a polychromatic spacially divergent beam and directed to a linear array of photovoltaic photodetectors with different spectral segments of the beam being intercepted by different photodetectors of the array. The signals from the photodetectors are separately and substantially simultaneously sampled and held to thereby obtain data usable for a high-accuracy wide-spectrum chromatogram.

22 Claims, 6 Drawing Figures

INSTANTANEOUS READING MULTICHANNEL POLYCHROMATIC SPECTROPHOTOMETER METHOD AND APPARATUS

BACKGROUND OF THE INVENTION

This invention relates to an improved polychromatic spectrophotometer method and apparatus which is particularly useful in the field of liquid chromatography in which a solvent solution carrying one or more materials to be analyzed is introduced into a chromatograph column, and the eluent issuing from the column is optically analyzed in a sample cell.

Chromatography has proved to be an extremely useful tool in both research and routine testing to provide rapid high accuracy chemical analysis. In a typical chromatographic procedure, the material whose composition is to be tested is dissolved in a solution consisting of one or more solvents, and is then pumped through a chromatographic column containing constituents such as silica or resins which cause different constituents of the material being tested to traverse the column at different predictable rates. The result is that different optical manifestations corresponding to the presence of different constituents are available for observation at different instants of time as the eluent issues from the chromatograph column.

One of the useful methods of obtaining readings from the chromatograph is by the use of a spectrophotometric detector which provides a chart of sample component separation in terms of radiation absorbance at what is essentially a single selected wavelength of radiation with which the sample is illuminated in a sample cell at the end of the chromatographic column. Stated in another way, the sample may be illuminated with a relatively broad spectrum of illumination (say in the ultraviolet region) and the radiation absorbance is recorded at only one wavelength, such as for instance at 255 nanometers. An absorbance versus time plot of this nature is illustrated in FIG. 1. In that figure, the various peaks signify the presence of various different chemical constituents which are detectable at the particular selected illumination wavelength, the height of each peak being a function of the concentration of the constituent represented by the peak and the degree of absorbance of illumination caused by the manifestation of that particular constituent.

Another extremely valuable output from a spectrophotometric detector used with a chromatograph is an output of the nature illustrated in FIG. 2 of the accompanying drawings which represents the absorbance vs wavelength when taken at a particular instant of time after initiation of the chromatographic separation. This is referred to as a spectral plot or spectrum. Until very recently, it was not possible to obtain such a plot except by stopping the flow of fluid through the column, mechanically scanning a monochrometer, and repeating the same cycle over and over, generating a different spectrum on each cycle. The problem with this procedure is that it is very time consuming, and accuracy may be compromised by minor variations in conditions from one test to another.

In recent years, so-called charge-coupled diode array spectrophotometric detectors have been used in liquid chromatography which attempt to produce the spectral plot corresponding to that of FIG. 2 in a single pass of the fluid through the liquid chromatography column, and without stopping the flow of fluid eluent. Such arrangements are described, for instance, in an article by Stuart A. Borman entitled "Charge-coupled Diode Array Detectors for LC" which appeared on pages 836A through 842A of "Analytical Chemistry" volume 55, number 8, July 1983.

Such charge-coupled diode array systems for liquid chromatography are attractive for what they attempt to do, but they suffer from a number of very serious problems and deficiencies. For instance, they are quite expensive and complicated in structure, slow in operation, offer a low signal-to-noise ratio, and a low accuracy, and a limited dynamic range. The charge-coupled diode arrays themselves are very expensive. The diodes in the array are back-biased so that they operate as capacitors in parallel with photoresistors. In some arrays, additional capacitors are built into the array.

Typically, in operation, all of the diode capacitors are charged to a uniform voltage level, and then discharged on the basis of illumination received, the charge-coupled diodes operating like photoresistors. The degree of discharge is thus supposed to be a measure of the amount of illumination received, and the degree of discharge is measured each time the device is strobed to recharge the capacitor. One very serious source of error is that it is very difficult to repeatedly recharge the devices to exactly the same level. Also, unfortunately, the devices have an appreciable dark discharge current which is subject to substantial change, particularly in response to changes in temperature. Accordingly, it is necessary to constantly recalibrate the diodes for dark discharge current by using mechanical shutters which darken the diodes, strobing all of the diodes to derive dark discharge values, storing those values, and then subtracting those dark discharge values from the subsequent readings during illumination. This limits accuracy and also creates a tremendous overhead in terms of digital storage space and processing time. It also slows down the total process and limits the number of scans available during a particular interval of time.

Thus, while the measurement scan is claimed to be as short as 1/100th of a second, the fastest claimed repeated sampling rate is only 25 times per second. Another major factor in reducing the overall speed of the charge-coupled diode system and increasing the overhead in terms of digital storage space and processing time is that the system is so lacking in accuracy that the results of four scans are taken and the individual readings of the four scans are averaged to provide a higher accuracy result. This accounts for the fact that the scan may take only 1/100th of a second, but the fastest sampling rate is only 25 times per second. Furthermore, the strobing of the devices in the charge-coupled diode array systems creates substantial "noise" (undesired signals) substantially reducing the so-called signal-to-noise ratio (the ratio of useful signals to noise signals).

The dynamic range of the devices is inherently limited on the upper end by the fact that there is only a certain amount of charge which can be discharged from each device in response to a strong optical signal. Unfortunately, the amount of charge which can be discharged from each device is seriously limited by the fact that the operation very soon gets into a nonlinear range as discharge proceeds. The range and accuracy are also limited on the low side because it is difficult to accurately measure a very small optical signal based upon the measurement of a small difference between two large quantities. Thus, the measurement involves measuring a difference between the total charge as reduced to a very minor extent by a small optical signal, and the subsequent recharge value.

The accuracy is further seriously limited by the fact that the acquisition of the data is carried out in a scan cycle which is too slow to capture the data for all of the spectral segments required for the spectral plot of the entire scan spectrum before the sample concentration in the sample cell changes appreciably because of the flow of eluent through the cell. If this source of inaccuracy is to be reduced, the eluent flow rate must be reduced, thus substantially reducing the efficiency of the system. Similarly, the rate at which successive total spectrum samples can be taken is typically a maximum of 25 per second, a rate which also may require a reduction in the eluent flow rate and a consequent reduction in efficiency of the system.

The above-mentioned *Analytical Chemistry* article indicates a clear recognition of many of the above-mentioned problems, including the high cost of the photodetector array, and the fact that the prior single wavelength and variable wavelength liquid chromatograph detectors are cheaper and inherently more sensitive than the charge-coupled diode detector array systems.

While the article mentions "simultaneously monitoring all wavelengths in the spectrum", it does not really operate "simultaneously" but, as discussed above, in a scan which takes at least 1/100th of a second, and typically more time up to $2\frac{1}{2}$ seconds.

SUMMARY OF THE INVENTION

It is an important object of the present invention to provide a very accurate and substantially instantaneous-reading multi-channel polychromatic spectrophotometer which is operable to rapidly take successive substantially instantaneous spectra.

Another object of the present invention is to accomplish all of the purposes which the charge-coupled diode array detector systems are supposed to accomplish in liquid chromatography, while substantially avoiding or overcoming each of the problems enumerated above.

Another object of the invention is to provide a polychromatic spectrophotometer for use in liquid chromatography which is comparable in accuracy and sensitivity to the best current single-wavelength and variable-wavelength liquid chromatography detectors.

Other objects and advantages of the invention will be apparent from the following description and the accompanying drawings.

In carrying out the invention in a preferred form thereof there is provided an improved widespectrum spectrophotometric detector method for substantially instantaneous polychromatic detection and storage of a plurality of spectral segments of radiation to be analyzed comprising directing a beam of radiation into a liquid sample cell containing a sample to be analyzed in solution, receiving illumination emanating from the sample cell as a result of the beam of radiation from the radiation source and diffracting the emanated radiation into a polychromatic spacially divergent beam, directing the divergent beam to a linear array of photodetectors with different spectral segments of the beam being intercepted by different photodetectors of the array, separately and substantially simultaneously sampling and holding signals from all of the photodetectors to thereby obtain data usable for a high-accuracy widespectrum chromatogram.

BRIEF DESCRIPTION OF THE DRAWINGS

FIG. 3 thus represents a combination of a number of FIG. 1 plots and a number of FIG. 2 plots.

DESCRIPTION OF PREFERRED EMBODIMENTS

Figure 1:
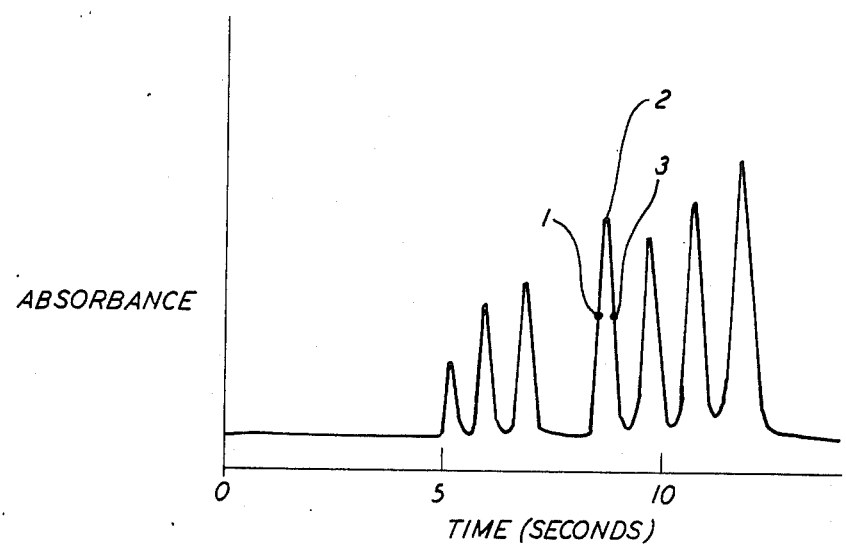
FIG. 1 is a plot of an absorbance vs time trace of the type which is produced by the present invention when employed with a liquid chromatograph and when detecting a single ultraviolet wavelength during passage of the eluent from the liquid chromatograph.

FIG. 1 illustrates a plot of absorbance versus time, which is of the kind obtainable presently with high accuracy single-wavelength, or variable-wavelength liquid chromatography detectors, and which may be obtained by the present invention when operated in a single-detector mode. In this plot, individual peaks such as peak 2 usually represent the presence of one distinctive constituent. As explained further below, comparison of spectra at corresponding positions 1 and 3 on the rising and falling side of the peak 2 assist in confirming the presence of a single constituent.

Figure 2:
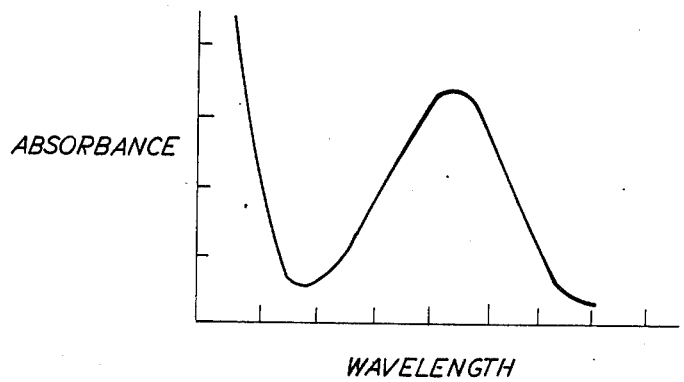
FIG. 2 illustrates a spectral plot obtainable from the apparatus of the present invention and representing absorbance over a substantial spectral range of illumination at a particular instant of time during the operation of a liquid chromatograph.

FIG. 2 illustrates a plot of absorbance versus wavelength (spectral plot) of the kind which may be obtained from the data acquired by the instantaneous-reading multichannel polychromatic spectrophotometer of the present invention. This is in essence a "snapshot" showing the absorbance condition of the sample over the entire wavelength range covered at a particular instant of time. It is one of the features of this invention that successive "snapshots" may be taken, or the data for such "snapshots" may be taken in rapid succession at a rate of more than 100 per second. Data may be extracted from these successive "snapshots" for plots corresponding to FIG. 1 at selected single wavelengths.

Figure 3:
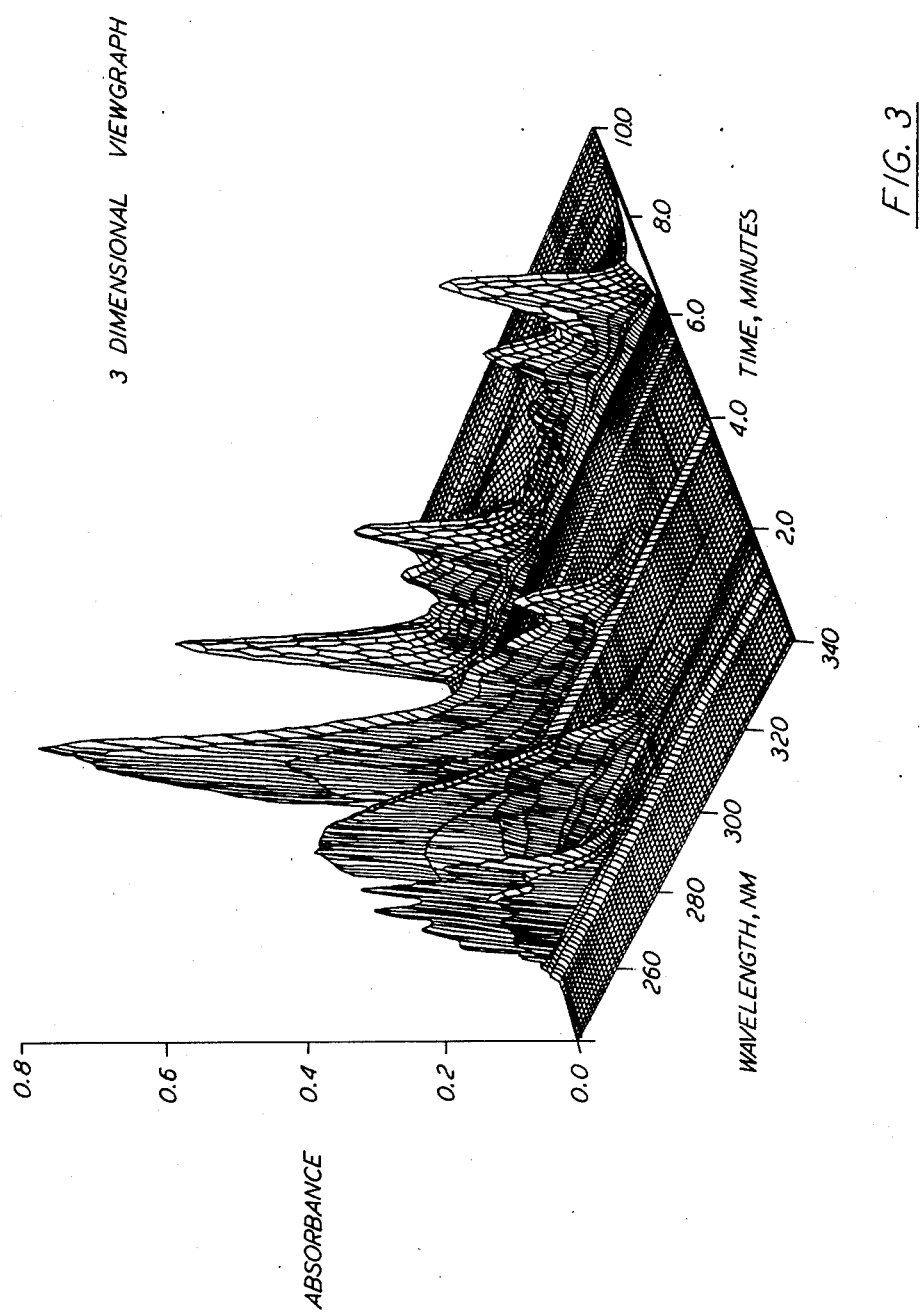
FIG. 3 is a three-dimensional representation of a number of plots corresponding to that of FIG. 1 at a number of different wavelengths, and thus represents all of the data which may be derived by the system of the present invention during a single pass of eluent through a liquid chromatographic column.

FIG. 3 shows how the data may also be used to produce multiple plots in three-dimensional mode to provide all of the information carried by FIG. 1 for the entire spectrum represented by FIG. 2. This is done in FIG. 3 simply by taking a series of the spectral plots, such as the plot of FIG. 2, which are taken at spaced time intervals. Alternatively this is done in FIG. 3 by plotting a series of the FIG. 1 plots for different wavelengths on the same plot diagram, with successive plots being displaced slightly upward and to the right on the plot paper to provide a three-dimensional effect. Other plotting methods are also available for presenting both the time plot information of FIG. 1 and the spectral plot information of FIG. 2 in a single figure.

Figure 4:
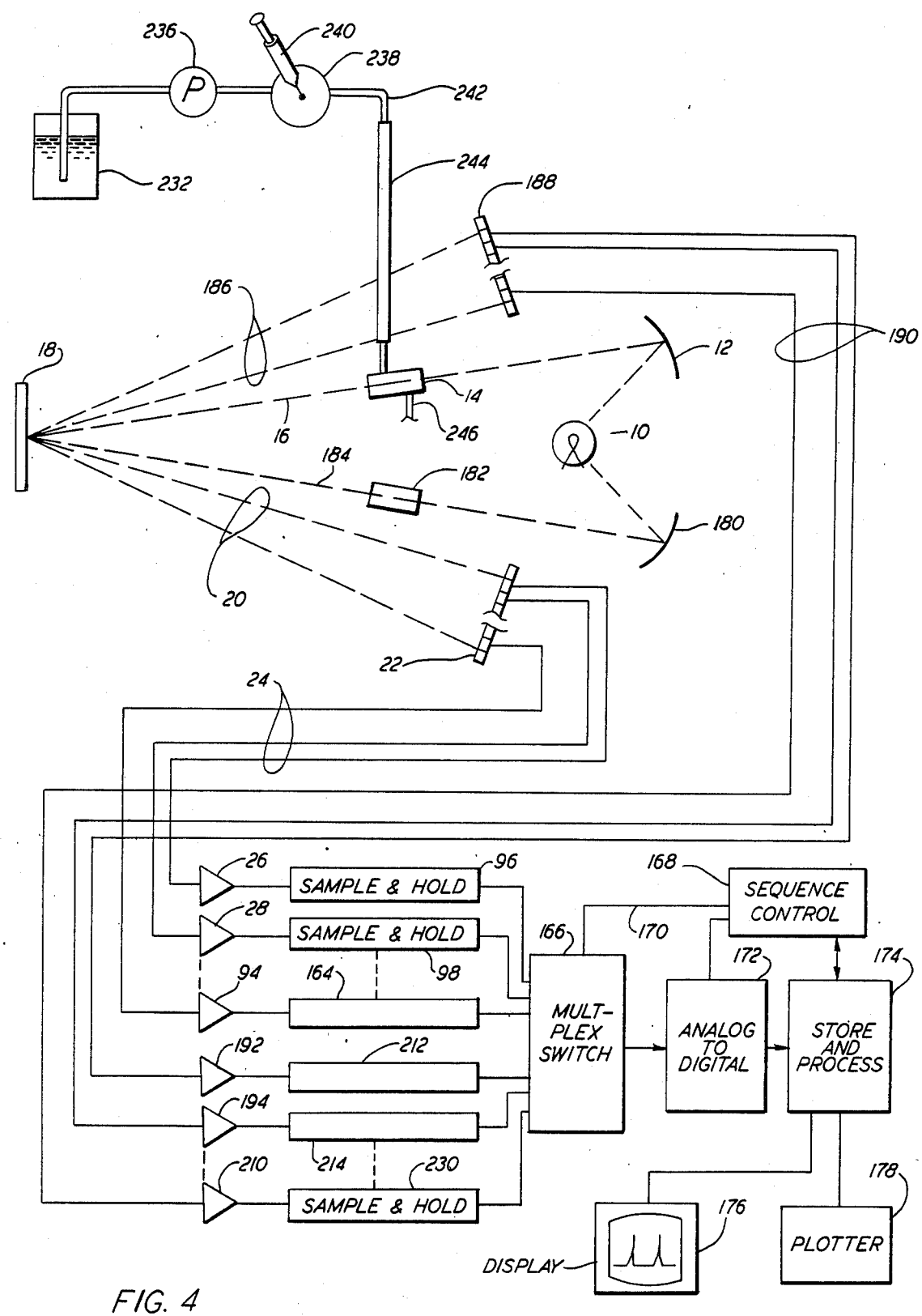
FIG. 4 is a schematic diagram of a liquid chromatograph system which carries out a preferred embodiment of the present invention.

Referring more particularly to the schematic diagram of FIG. 4, radiation from a radiation source such as a deuterium lamp 10 is directed to a reflector 12 and then through a sample cell 14 containing a sample of a material to be analyzed in solution. The result is that illumination is emanated from the sample cell, as indicated at 16, which is modified by the contents of the sample cell. For instance, certain wavelengths of the radiation entering the cell may be partially absorbed by the contents of the cell 14. The radiation 16 emanating from the cell 14 is directed to a diffraction grating 18 which diffracts the emanated radiation into a polychromatic spacially divergent beam indicated at 20 and directs the divergent beam to a linear array 22 of photodetectors. Different spectral segments of the beam are intercepted by different photodetectors within the array 22. The signals from all of the photodetectors 22 are separately and substantially simultaneously sampled and held to thereby obtain data usable for a high-accuracy wide-spectrum chromatogram.

To accomplish this purpose, the signals from the photodetectors are carried through separate signal channels including connections 24 to amplifiers 26, 28, and 94, and from the amplifiers to sample-and-hold circuits 96, 98, and 164. As indicated by the missing numbers, not all of the connections 24, amplifiers, and sample-and-hold circuits are illustrated. It is anticipated for instance that there will be typically 35 photodetectors in the array 22, with 35 associated amplifiers 26–94, and 35 sample-and-hold circuits 96–164.

The sample-and-hold circuits 96-164 are controlled by a multiplex switch 166 operating in response to control signals from a sequence control 168 through connection 170. The multiplex switch 166 causes the sample-and-hold circuits 96-164 to simultaneously sample, then to stop sampling and simultaneously "hold", and then to cause a sequential read-out of the analog quantities represented by those signals for conversion from analog to digital form in an analog-to-digital converter 172. Converter 172 is also controlled by the sequence control 168. The resultant digital data is then stored and processed in what is shown as a schematically combined data storage and data processing unit 174. As a result, under the control of unit 174, and as an output from unit 174, plots such as those illustrated in FIGS. 1 and 2 may be displayed on a cathode ray tube display 176, or plotted on a plotter 178. Unit 174 may be a conventional digital computer, including digital storage as well as digital processing.

A feature of the invention which is preferred, but not necessarily essential, and which is illustrated in FIG. 4, is the provision of a second beam from lamp 10 which is directed to a reflector 180, and through a reference cell 182 for deriving signals which may be used for compensating the operation of the system for variations such as flicker and aging the radiation source. The reference cell 182 will usually contain air, but may contain liquid solvents similar to the solvents in the solution of the sample cell 14. The radiation emanating from the reference cell 182, as indicated in 184, is directed to the grating 18 and is diffracted into a polychromatic spacially divergent beam 186 corresponding to the beam 20 and directed to a second linear array 188 of photodetectors. Photodetectors 188 are connected by means of conductors 190 to amplifiers 192, 194, 210 and thus to sample-and-hold circuits 212, 214, and 230.

While only three signal channels associated with the sample-and-hold circuits 212, 214, and 230 are shown, a total of ten channels are preferably provided. While the array 188 is preferably identical to the array 22, the cells of array 188 are preferably arranged together in groups, and the members of each group connected in parallel to a single amplifier 192 or 194 or 210. These grouped and paralleled signals provide sufficient compensation of the signals from array 22 for system variations such as variations in the output of lamp 10.

The paralleled outputs of a particular group are used to compensate or standardize signals from each of the photocells of array 22 corresponding to the members of that group. The paralleling of the photocells in array 188 can be used to compensate for the fact that the illumination in the reference channel can be less than the illumination which is sent to the photocells of array 22 due to the beam splitting method. The signals held in the sample-and-hold circuits 212, 214, and 230 are processed by the multiplex switch 166 and the analog-to-digital converter 172 in exactly the same way as the previously described signals. These signals are also stored and processed by the unit 174, but are used there to compensate the signals received through the sample-and-hold circuits 96, 98, 164. The photodetectors in the arrays 22 and 188 are all preferably photovoltaic cells which are operated in a current delivery mode to feed the associated amplifiers.

The greatest utility for the subject invention is in liquid chromatography. The elements of a liquid chromatography apparatus are illustrated schematically in conjunction with the sample cell 14. They include a reservoir 232 for a solvent which may consist of one or more solvent liquids. A pump 236 is provided for pumping the solvent from the reservoir 232 through an injector valve 238. A known volume of the material which is to be tested is injected into the solvent through a syringe 240 at the injection valve 238, and the pressure of the pump forces the solvent with the solute through a connection 242 and into and through a chromatograph column 244, which terminates in the sample cell 14. An exhaust connection is provided, as indicated at 246, to carry the spent eluent to a sump, not shown.

The representation of the optics in FIG. 4 has been idealized for clarity in presentation. For instance, the optical components including the lamp 10, the reflectors 12 and 180, the sample cell 14 and the reference cell 182, and the issuing beams of radiation 16 and 184 should have their center lines all substantially contained within a single plane, and that plane should be rotated 90 degrees to be substantially perpendicular to the surface of the drawing figure in order to represent the system in a more accurate sense from the standpoint of the optics of the system.

Figure 5:
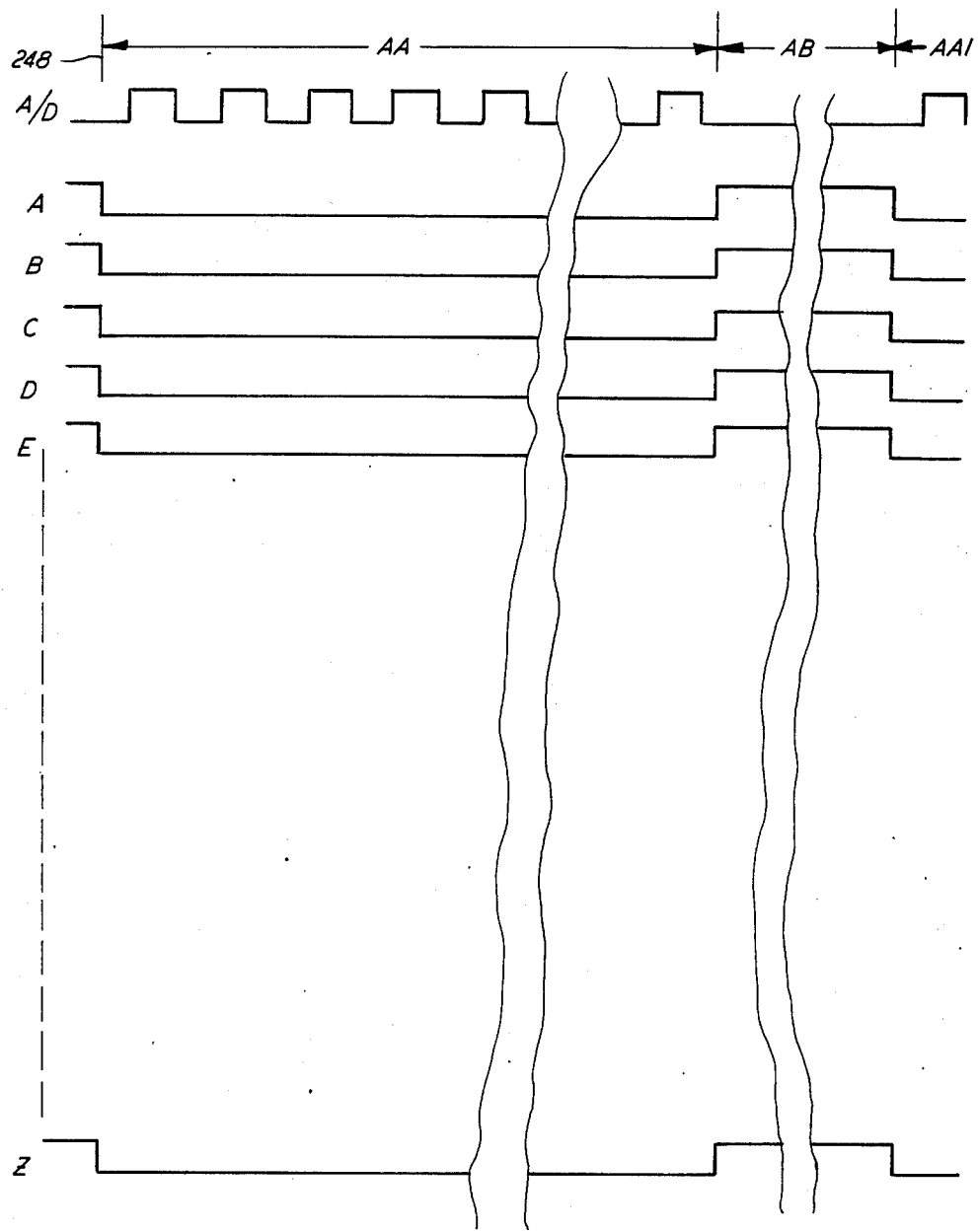
FIG. 5 is a timing diagram illustrating one preferred mode of operation of the system of FIG. 4 in which signal samples are taken simultaneously.

There are two basic preferred modes of operation of the apparatus of FIG. 4 which are illustrated in FIGS. 4 and 5 respectively. In the first preferred operation illustrated in FIG. 5, all of the sample-and-hold circuits are caused to stop sampling and commence holding at the same instant. The operation of the sample-and-hold circuits is illustrated in curves A, B, C, D, E, and Z in FIG. 6, and the point in time at which all of these sample-and-hold circuits commence the "hold" operation is indicated at time marker 248, which is the beginning of an interval labelled AA at the top of FIG. 5. The "hold" interval continues for the entire interval AA, at which time all of the circuits begin the "sample" operation which continues for an interval AB. Another "hold" operation then begins, as indicated at AA1.

During the entire hold interval AA, the analog-to-digital converter 172 operates in a sequence to read out the signals on the separate channels which are being held by the sample-and-hold circuits and to convert those signals to digital signals. The operation of the analog-to-digital converter 172 is carried out under the control of the multiplex switch 166, and the timing of the operation of the analog-to-digital converter is illustrated by the curve marked A/D in FIG. 5. Each positive square pulse of that curve represents one analog-to-digital conversion. The entire operation is very rapid. For instance, in the preferred embodiment of this invention, the analog-to-digital conversion pulses may commence in succession every 80 microseconds and persist for 35 microseconds. On this schedule, all 45 of the sample-and-hold circuits may have their output signals converted in only 3,600 microseconds or 3.6 milliseconds. The sample interval AB then commences for all of the sample-and-hold circuits. The sample interval AB may continue for a similar time period of 3.6 milliseconds, and then the next hold and analog-to-digital conversion interval AA1 commences.

The combination of the interval AA plus the interval AB therefore represents a complete data acquisition cycle which can be used to produce a spectral chromatogram. This cycle may be repeated immediately, and as often as desired. As described, the cycle lasts for 7.2 milliseconds, which means that 138 data acquisition cycles can be completed in every second. By contrast, the fastest data acquisition cycle for the charge-coupled diode array detectors is 25 per second.

During the interval AB, while the sample-and-hold circuits are sampling, the store-and-process unit 174 is carrying out the data processing functions to derive the refined data from the last read-out for display on the display unit 176 or plotting on the plotter 178, or for storage in a more permanent memory for future recall and processing or comparison with other measurements. The refining of the data by unit 174 typically includes such operations as (a) conversion from "percent of radiation transmission" to "absorbance", and (b) digital filtering.

Figure 6:
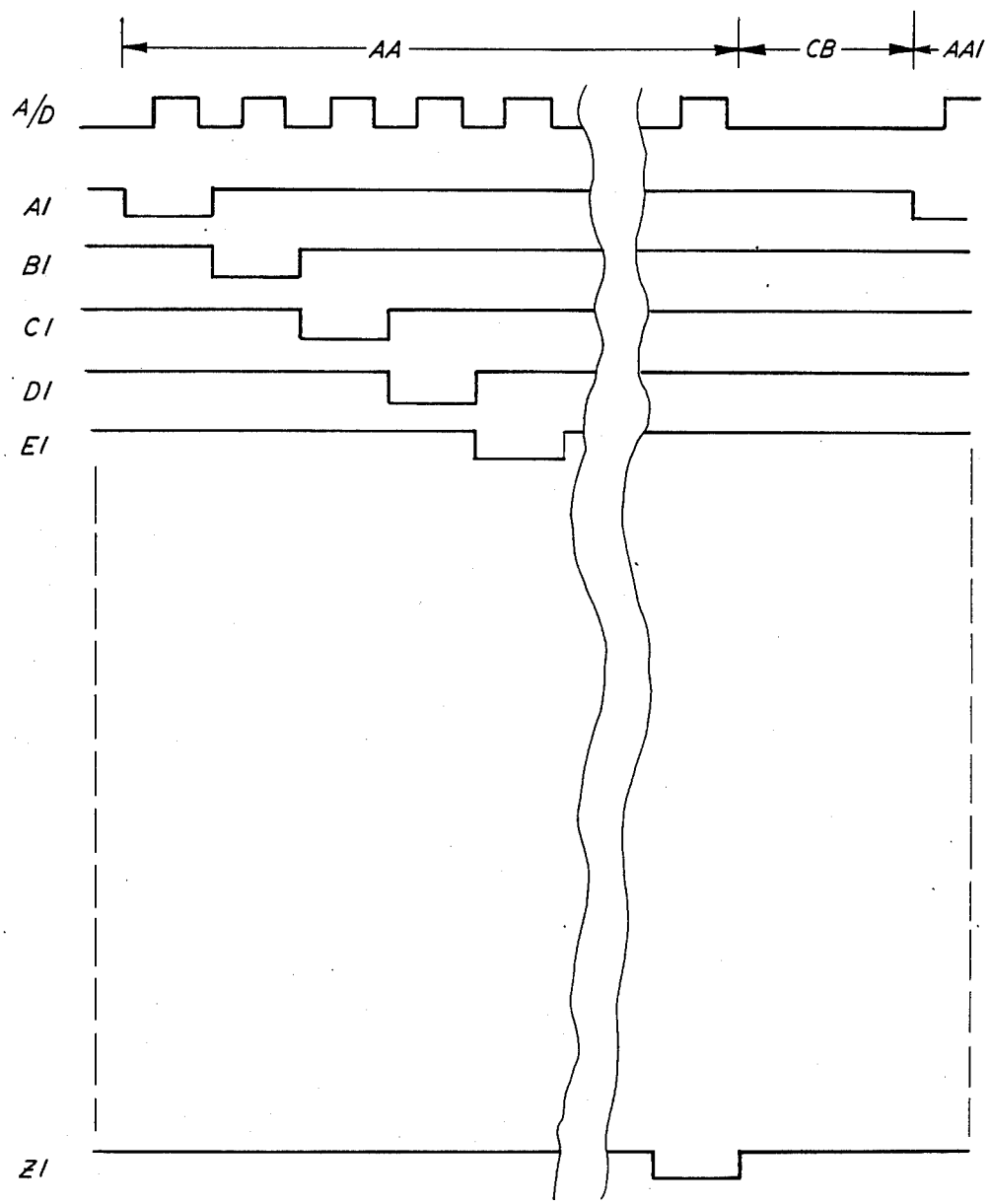
FIG. 6 is a timing diagram illustrating a second preferred mode of operation in which signals are sampled in sequence, but in such a rapid sequence that they are taken substantially simultaneously.

FIG. 6 represents another preferred mode of operation of the apparatus of FIG. 4 in which the sample-and-hold circuits operate in a sequence, rather than simultaneously. However, the entire sequence of operation is carried out with such rapidity, within 3.6 milliseconds, that it is referred to as "substantially simultaneous". This arrangement has the virtue that while one sample-and-hold circuit is in a "hold" mode, and having its output converted from analog to digital, all of the other sample-and-hold circuits are continuing in the sample mode. An extended sample mode is desirable in order to increase the integration time of the signal during the sampling interval in order to promote accuracy. The series resistance and shunt capacitance of the circuits provide an adequate approximation to the desired integration function. However, useing active circuitry, a true, resetting-type integration function can be provided for optimum theoretical results. Thus, in the embodiment of FIG. 6, the analog-to-digital conversion proceeds at the same rate as in the embodiment of FIG. 5, during time interval AA, but the successive analog-to-digital conversion times are used for brief individual sampling intervals.

The result is that the timing of the total cycle can be shortened, and the accuracy increased, by extension of each sampling interval. An interval CB may still be provided for reading the analog-to-digital converted data transferred to the store-and-process circuit 174 out of data buffer registers in that component, and for accomplishing any other necessary digital processing, before commencing another cycle of analog-to-digital conversions. An interval of 1.52 milliseconds has been found to be quite adequate for interval CB. Thus, the total cycle, including intervals AA and CB, in this process embodiment, may be 5.12 milliseconds, providing a capability for 195 cycles per second. However, most, if not all of the software tasks required during this mode of system operation (i.e. data acquisition) can be accomplished during the time interval after the actual conversion is completed, but during which the individual channel conversion window is still open (a typical system will provide 25 microseconds for this purpose.) In the limit, this obviates the necessity for the 1.52 milliseconds allotted above. With such a reduction, the cycle time becomes 3.6 milliseconds or a cycling rate equivalent to 278 cycles per second. This is essentially an eleven-fold increase in cycle timing speed over the highest speed for the charge-coupled diode array spectrophotometer detector systems.

In both of the methods illustrated in FIGS. 4 and 5, the complete set of data may be taken, converted from analog to digital form, and processed, in a very brief interval. That interval can be repeated 135 times per second with the operation of FIG. 5, and up to 278 times per second with the operation of FIG. 6. Thus, it is preferred that the sequence interval should be no more than 1/100th of a second. These methods may be employed with a high-speed liquid chromatograph, without the necessity for slowing down the flow of eluent to take readings.

An important feature of the present invention is the discovery that very accurate and useful spectral mode scans (such as illustrated in FIG. 2) can be obtained on the basis of a sampling of only 35 spectral segments. Taking data from only 35 spectral segments, or even less, provides major advantages in reducing the processing time and in reducing the data handling "overhead" of taking and processing a large number of segments. The resultant curve plotted from the 35 points is preferably smoothed so that the 35 distinct data points are not evident in the output curve. Such smoothing is preferably accomplished within the store-and-process unit 174 of FIG. 4 by digital data manipulation. Various known mathematical methods can be employed for filling in a smooth curve between successive points. The use of only about 35 points for providing a spectral scan is surprising in the context of the field of chromatography. Chromatographers normally think in terms of extremely fine spectral resolution. For instance, the charge-coupled device array systems typically require at least 100 detectors, and more typically 250 to 500 detectors, apparently in an attempt to achieve high resolution. Thus, it is preferred to employ an array of about 35 detectors, or less, and preferably no more than 40 detectors for the usual spectral scan. With 35 detectors, in a preferred embodiment, the individual spectral segments intercepted by individual photodetectors each preferably cover a wavelength range of about five nanometers. Thus, when used in the ultraviolet, the total range coverage for 35 detectors may extend from 190 nanometers to 365 nanometers in five-nanometer spectral segments.

One of the most important modes for practical utilization of the spectral scan, such as pictured in FIG. 2, is to compare the spectral scan at a point in time corresponding to a point on the rising edge of a time scan peak, such as at point 1 on peak 2 in FIG. 1, with a spectral scan taken at a corresponding moment in time on the falling side, as indicated at 3. If the two spectral scans coincide closely, there is a confirmation that the peak 2 is representative of a single constituent. However, if the spectral scans do not coincide, it is a strong sign that another constituent is contributing to the peak, and the analysis must be further refined. One of the most serious problems with the charge-coupled diode array systems is that the considerable length of time required for scanning the array of detectors not only creates a serious distortion, but the distortion on the rising side of a peak is different from the distortion on the falling side of the peak. Accordingly, the accumulation of the two different distortions makes the two spectral scans very difficult to compare accurately. By contrast, the system of the present invention, with the fast scanning rate (instantaneous in the method of FIG. 5 and substantially instantaneous in the method of FIG. 6) provides highly consistent and reproducible spectral scans for accurate comparisons. As used in this specification, and in the appended claims, the term "substantially instantaneous" is understood to include "instantaneous".

Various photovoltaic device arrays can be used for the arrays 22 and 188 in carrying out the present invention. However, it is preferred to employ a linear array of PN junction silicon photovoltaic detectors supported upon a single substrate. One very satisfactory array of this description is available under product number S1592-01 from Hamamatsu Corporation, 420 South Avenue, Middlesex, N.J. 08846. That array was originally designed for a multichannel spectrophotometer system of the kind in which only one or two channels are used at a time. Fortunately, this array is also very practical for use in the present system.

Another important advantage of providing a limited number of photodetectors in the array is that the photodetector area of individual photodetectors is more nearly square in shape to receive and respond to an optically created image of the exit aperture of the sample cell 14, which is typically circular. In the present system, such an aperture is preferably provided, and imaged at the array.

For instance, in the above-mentioned commercially available Hamamatsu array, the ratio of the length of each element along the array to the width of each element is about 1 to 4.5, whereas in the charge-coupled device arrays, the corresponding ratio is about 1 to 10. This is another respect in which the arrangement of the present invention is superior.

The present invention has been described so far primarily in terms of detectors which detect optical absorbance in the ultraviolet region. However, the teachings of the invention may be employed with detector systems operating in the visible radiation region, and to detect fluorescence instead of absorbance. Furthermore, these modes of detection may be employed with all of the various known techniques of liquid chromatography in which the results are detectable by absorbance or fluorescence. When the system is used as an ultraviolet absorbance detector, it is preferably operated in a wavelength range from about 190 to 364 nanometers. When operated as a fluorescence detector, it may typically operate to detect fluorescence emissions in a range from 300 to 475 nanometers in wavelength, or alternatively in a range from 425 to 600 nanometers in wavelength.

While only one analog-to-digital converter 172 is disclosed in FIG. 4, it is obvious that the provision of additional analog-to-digital converters which could operate at the same time would further speed up the operation of the entire system.

While the operating sequences illustrated in FIGS. 4 and 5, and described above, represent preferred operating sequences for the system of the invention, the apparatus of the present invention may be operated in other sequences, if desired. Thus, it is one of the features and advantages of the invention that the scanning of the various different sample-and-hold circuits may be selectively programmable to provide a still faster rate of scan (when a long sample period is not required), or the sampling interval may be increased, if desired for greater precision. Furthermore, the system may be programmed to look at only one or several selected spectral segments, or to skip around from one segment to another in any desired order, and to generate ratios, differences, and sums of the various signals. By contrast, the charge-coupled diode array systems do not have this flexibility because the charge-coupled diodes all must be scanned at a fixed rate which is not too fast and not too slow, but which does not provide the selectively programmable flexibility of the present system.

Furthermore, the present system may be operated without the sample-and-hold feature. The signals from the photovoltaic photocells are then continuously measured. This mode of operation is especially effective if only a single spectral sector is to be monitored at a time. This is a mode of operation which is not at all available with the prior charge—coupled diode array systems. This is a very important point because the fixed timing sequence of the charge-coupled diode array systems is not at all suited to many chromatography operating conditions.

In further comparing the present system with the prior charge-coupled diode array systems, the array itself for the present system is about one tenth the cost of the more complex charge-coupled diode array, and the cost of the overall system is about one fourth the cost of the charge-coupled diode array systems. At the same time, the system of the present invention provides a signal-to-noise ratio improvement of about ten to one, in addition to providing for a much faster data rate (substantially simultaneous).

The present invention provides performance results which are comparable to the prior, highly accurate, single and variable wavelength detectors so that the product may logically replace the single and variable wavelength detectors which are presently in use. By contrast, as mentioned in the aforementioned article in "Analytical Chemistry" by Stuart Borman, the charge-coupled diode array systems are predicted never to replace the single wavelength and variable wavelength liquid chromatography detectors because they are too expensive and not sensitive enough.

Because of the greater simplicity of the present invention over the prior charge-coupled diode array systems, the programs employed in the store-and-process unit 174 may be much simpler than the computer programs required for the other systems in order to prepare and display the resulting spectral information. Furthermore, there is a corresponding reduction in data processing time and capacity which is required. This is true also of the software programs to determine peak purity and peak identity from the spectral data.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. An improved wide-spectrum spectrophotometric detector method for substantially instantaneous polychromatic detection and storage of a plurality of spectral segments of radiation to be analyzed comprising directing a beam of radiation into a liquid sample cell containing a sample to be analyzed in solution, receiving illumination emanating from the sample cell as a result of the beam of radiation from the radiation source and diffracting the emanated radiation into a polychromatic spacially divergent beam, directing the divergent beam to a linear array of photodetectors with different spectral segments of the beam being intercepted by different photodetectors of the array, separately and substantially simultaneously sampling and holding signals from all of the photodetectors so as to obtain data usable for creating a high-accuracy wide-spectrum chromatogram.

2. A method as claimed in claim 1 for use with a liquid column chromatograph and wherein the liquid sample cell is connected to the bottom of the liquid chromatograph column and wherein the signals from all of the photodetectors of the array are simultaneously sampled and held and then sequentially converted from analog to digital form for further processing and analysis.

3. A method as claimed in claim 1 for use with a liquid column chromatograph with the liquid sample cell connected to the bottom of the liquid chromatograph column and wherein the signals from all of the photodetectors of the array are simultaneously sampled and held and then sequentially converted from analog to digital form for further processing and analysis and wherein all of the previously recited steps are repeated in a sequence during operation of the liquid chromatograph.

4. A method as claimed in claim 1 for use with a liquid column chromatograph and wherein the liquid sample cell is positioned and arranged at the bottom of the liquid chromatograph column and wherein the signals from the different photodetectors of the array are substantially simultaneously sampled and held by sequentially sampling and holding all of the signals in a time interval of less than 0.01 second and wherein the signals are all converted from analog to digital form in synchronism with the sample-and-hold operation within the said time interval.

5. An improved wide-spectrum spectrophotometer which is operable for substantially instantaneous polychromatic detection and storage of a plurality of spectral segments of radiation to be analyzed comprising a liquid sample cell for containing a sample to be analyzed in solution, a radiation source means for directing a beam of radiation into said sample cell, a diffraction means positioned and arranged to receive illumination emanating from said sample cell as a result of said beam of radiation from said radiation source means, said diffraction means being operable to diffract the emanated radiation into a polychromatic spatially divergent beam, a linear array of photodetectors positioned and arranged to intercept said polychromatic beam with different spectral segments of said beam being intercepted by different photodetectors of said array, a separate signal channel means for each of said photodetectors, each of said signal channel means including a sample-and-hold circuit connected to receive and store signals from each photodetector of said array, control means operable to substantially simultaneously actuate said separate signal channel means and said sample-and hold circuits for all of said photodetectors, analog to digital conversion means connected to said sample-and-hold circuits and operable in response to said control means for converting the held signals to digital form, and digital data storage and processing means connected to receive and store and process the converted stored signals so as to provide spectra analysis information.

6. A spectrophotometer as claimed in claim 5 wherein each of said photodetectors is a photovoltaic device.

7. A spectrophotometer as claimed in claim 6 for operation in the ultraviolet portion of the spectrum wherein said photodetectors are adapted to respond to ultraviolet radiation.

8. A spectrophotometer as claimed in claim 7 wherein said radiation source means comprises a deuterium lamp together with optical elements for directing the beam of radiation to said sample cell.

9. A spectrophotometer as claimed in claim 6 for operation in the fluorescent mode wherein said radiation source means is adapted to excite a fluorescent condition in constituents to be detected and analyzed within said sample cell and wherein said photodetectors are positioned and arranged with respect to said diffraction means to intercept spectral segments within a range of wave lengths at which the fluorescent constituents in the sample cell are expected to fluoresce.

10. A spectrophotometer as claimed in claim 6 wherein each photodetector photovoltaic device is a PN junction device.

11. A spectrophotometer as claimed in claim 10 wherein the PN junction devices are formed and arranged together upon a single substrate.

12. A spectrophotometer as claimed in claim 5 which is combined with a liquid chromatograph column and in which said sample cell is connected at the lower end of the liquid chromatograph column.

13. A spectrophotometer as claimed in claim 12 wherein said control means is operable to simultaneously actuate said separate signal channel means and said sample-and-hold circuits for all of said photodetectors, and wherein said control means is operable to control said analog-to-digital conversion means to convert the held signals to digital form in sequence.

14. A spectrophotometer as claimed in claim 12 wherein said control means is operable to substantially simultaneously actuate said separate signal channel means and said sample-and-hold circuits for all of said photodetectors by actuating said signal channel means and said sample-and-hold circuits in a sequence, and wherein said control means causes said analog-to-digital conversion means to operate in synchronism with the sequential operation of said separate signal channel means and said sample-and-hold circuits to convert the held signals to digital form in sequence.

15. A spectrophotometer as claimed in claim 14 wherein the duration of said sequence is no greater than 1/100th of a second.

16. A spectrophotometer as claimed in claim 5 wherein said diffraction means comprises a diffraction grating.

17. A spectrophotometer as claimed in claim 5 wherein each of said signal channel means for said photodetectors includes a separate amplifier means.

18. A spectrophotometer as claimed in claim 5 wherein the number of photodetectors in said array is no greater than 40.

19. A spectrophotometer as claimed in claim 18 wherein the number of photodetectors in said array is about 35.

20. A spectrophotometer as claimed in claim 5 wherein a second linear array of photodetectors is provided and wherein a reference cell containing a liquid similar to the sample cell liquid is provided, and wherein a means is provided for directing a portion of the radiation from said radiation source in a beam through said reference cell, a second diffraction means positioned and arranged to receive illumination emanating from said reference cell as a result of said beam radiation directed into said reference cell said from radiation source means, said second diffraction means being operable to diffract the emanated radiation into a second polychromatic spacially divergent beam corresponding to the beam resulting from the diffraction of radiation directed through said sample cell, said second linear array of photodetectors being arranged to intercept said second polychromatic beam with different spectral segments of said second beam being intercepted by different photodetectors of said second array, separate signal channel means for said photodetectors of said second array, each of said signal channel means including a sample-and-hold circuit connected to receive and store signals from each of said photodetectors of said second array, said control means being operable to actuate said signal channel means and said sample-and-hold circuits for all of said photodetectors of said second array substantially simultaneously with the actuation of said signal channel means and said sample-and-hold circuits for the first-mentioned array, said analog-to-digital conversion means being connected to said sample-and-hold circuits of said second array and operable in response to said control means for converting the held signalss to digital form for comparing the held signals from said second array with the held signals from said first array for compensating the operation of the system for optical variations in the radiation source.

21. A spectrophotometer as claimed in claim 20 wherein said second diffraction means is combined with said first-mentioned diffraction means.

22. A spectrophotometer as claimed in claim 21 wherein said signal channel means for said second array of photodetectors are fewer in number than the photodetectors in said second array and wherein said photodetectors of said second array are arranged in contiguous member groups with the members of each group being connected in parallel to an associated single signal channel means.

* * * * *